(12) United States Patent
Sekiguchi (10) Patent No.: US 9,775,540 B2
(45) Date of Patent: Oct. 3, 2017

(54) ENDOSCOPE INSERTION SHAPE OBSERVATION PROBE

(71) Applicant: OLYMPUS CORPORATION, Tokyo (JP)

(72) Inventor: Masahiko Sekiguchi, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 27 days.

(21) Appl. No.: 15/140,688

(22) Filed: Apr. 28, 2016

(65) Prior Publication Data

US 2016/0235338 A1    Aug. 18, 2016

Related U.S. Application Data

(63) Continuation of application No. PCT/JP2015/057465, filed on Mar. 13, 2015.

(30) Foreign Application Priority Data

Jul. 29, 2014    (JP) .................................. 2014-154071

(51) Int. Cl.
    *A61B 1/00*   (2006.01)
    *A61B 5/06*   (2006.01)
    (Continued)

(52) U.S. Cl.
    CPC .......... *A61B 5/062* (2013.01); *A61B 1/00043* (2013.01); *G02B 23/2476* (2013.01); *A61B 2034/2051* (2016.02)

(58) Field of Classification Search
    USPC ........................................................ 600/117
    See application file for complete search history.

(56) References Cited

U.S. PATENT DOCUMENTS 5,997,473 A    12/1999 Taniguchi et al.
6,745,065 B2 *  6/2004 Niwa ................. A61B 1/00128
                                               600/117
(Continued)

FOREIGN PATENT DOCUMENTS

JP    H64-009689 A    1/1989
JP    H06-082770 U    11/1994
(Continued)

OTHER PUBLICATIONS

International Search Report dated Jun. 2, 2015 issued in PCT/JP2015/057465.

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

An endoscope insertion shape observation probe that is elongatedly formed along a longitudinal axis direction and is insertable into a channel provided in an endoscope insertion section or is incorporated in the endoscope insertion section includes an electronic component, a housing section having a recessed shape that houses the electronic component, a pair of electric connection sections provided in the housing section, a pair of electric connection terminal sections provided in the electronic component and engaged with and electrically connected to the electric connection sections, the electric connection terminal sections mechanically holding the electronic component in the housing section, a groove section formed in the housing section, and two attaching-direction defining terminal sections provided in the electronic component, the attaching-direction defining terminal sections engaging into the groove section and defining a direction around a longitudinal axis in which the electronic component is attached to the housing section.

7 Claims, 10 Drawing Sheets

(51) Int. Cl.
*G02B 23/24* (2006.01)
*A61B 34/20* (2016.01)

(56) References Cited

U.S. PATENT DOCUMENTS

| | | | | |
|---|---|---|---|---|
| 7,648,458 B2 * | 1/2010 | Niwa | ..................... | A61B 5/06 |
| | | | | 600/117 |
| 8,801,602 B2 * | 8/2014 | Sekiguchi | .......... | A61B 1/00158 |
| | | | | 600/117 |
| 9,232,985 B2 * | 1/2016 | Jacobsen | ................ | A61B 5/062 |
| 2013/0317355 A1 * | 11/2013 | Jacobsen | ................ | A61B 5/062 |
| | | | | 600/424 |
| 2014/0039258 A1 * | 2/2014 | Sekiguchi | .............. | A61B 5/062 |
| | | | | 600/117 |
| 2014/0100463 A1 | 4/2014 | Sekiguchi et al. | | |

FOREIGN PATENT DOCUMENTS

| | | | |
|---|---|---|---|
| JP | 2580607 | B2 | 2/1997 |
| JP | H10-075929 | A | 3/1998 |
| JP | 2011-253644 | A | 12/2011 |
| JP | 5319859 | B1 | 10/2013 |
| JP | 5444522 | B1 | 3/2014 |
| WO | WO 2013/039059 | A1 | 3/2013 |
| WO | WO 2014/010288 | A1 | 1/2014 |

\* cited by examiner

ENDOSCOPE INSERTION SHAPE OBSERVATION PROBE

CROSS REFERENCE TO RELATED APPLICATION

This application is a continuation application of PCT/JP2015/057465 filed on Mar. 13, 2015 and claims benefit of Japanese Application No. 2014-154071 filed in Japan on Jul. 29, 2014, the entire contents of which are incorporated herein by this reference.

BACKGROUND OF THE INVENTION

1. Field of the Invention

The present invention relates to an endoscope insertion shape observation probe and, more particularly, to an endoscope insertion shape observation probe mounted with a plurality of magnetic coils.

2. Description of the Related Art

There has been known an endoscope insertion shape observation apparatus for displaying, on a monitor, an insertion shape of an endoscope inserted into a subject.

For example, International Publication No. 2013-039059 discloses an endoscope insertion state detecting apparatus in which a plurality of coil units are provided in an endoscope insertion shape observation probe disposed in an endoscope insertion section and magnetic fields generated by the plurality of magnetic coil units are detected by magnetic-field detecting means provided outside an endoscope.

Such a conventional endoscope insertion state detecting apparatus calculates positions in a three-dimensional space of the respective magnetic coil units of the endoscope insertion shape observation probe from the detected magnetic fields, determines a shape of the endoscope insertion section according to the positions of the magnetic coil units and estimation of an interval among the respective positions, and displays the shape on a monitor.

In the conventional endoscope insertion shape observation probe, a plurality of magnetic coil units obtained by winding thin copper wires around iron cores are disposed in a tube at an interval and configured as one elongated endoscope insertion shape observation probe.

SUMMARY OF THE INVENTION

An endoscope insertion shape observation probe according to an aspect of the present invention is an endoscope insertion shape observation probe that is elongatedly formed along a longitudinal axis direction and is insertable into a channel provided in an endoscope insertion section or is incorporated in the endoscope insertion section. The endoscope insertion shape observation probe includes: an electronic component; a housing section having a recessed shape that houses the electronic component; a pair of electric connection sections provided in the housing section; a pair of electric connection terminal sections provided in the electronic component and engaged with and electrically connected to the electric connection sections, the electric connection terminal sections mechanically holding the electronic component in the housing section; a groove section formed in the housing section; and two attaching-direction defining terminal sections provided in the electronic component, the attaching-direction defining terminal sections engaging into the groove section and defining a direction around a longitudinal axis in which the electronic component is attached to the housing section.

According to the present invention described above, it is possible to provide an endoscope insertion shape observation probe in which setting of a plurality of magnetic coils is simplified and assemblability and maintainability are improved and maintenance costs can be reduced.

DETAILED DESCRIPTION OF THE PREFERRED EMBODIMENTS

An embodiment of the present invention is explained below with reference to the drawings.

Note that an endoscope insertion shape observation probe according to the embodiment of the present invention is explained. However, in the following explanation, among the drawings based on respective embodiments, some drawings are schematic. Therefore, relations between thicknesses and widths of respective portions, ratios of the thicknesses of the respective portions, and the like include those different from real ones. Portions having relations of dimensions and ratios different from one another are sometimes included among the drawings.

Figure 1:
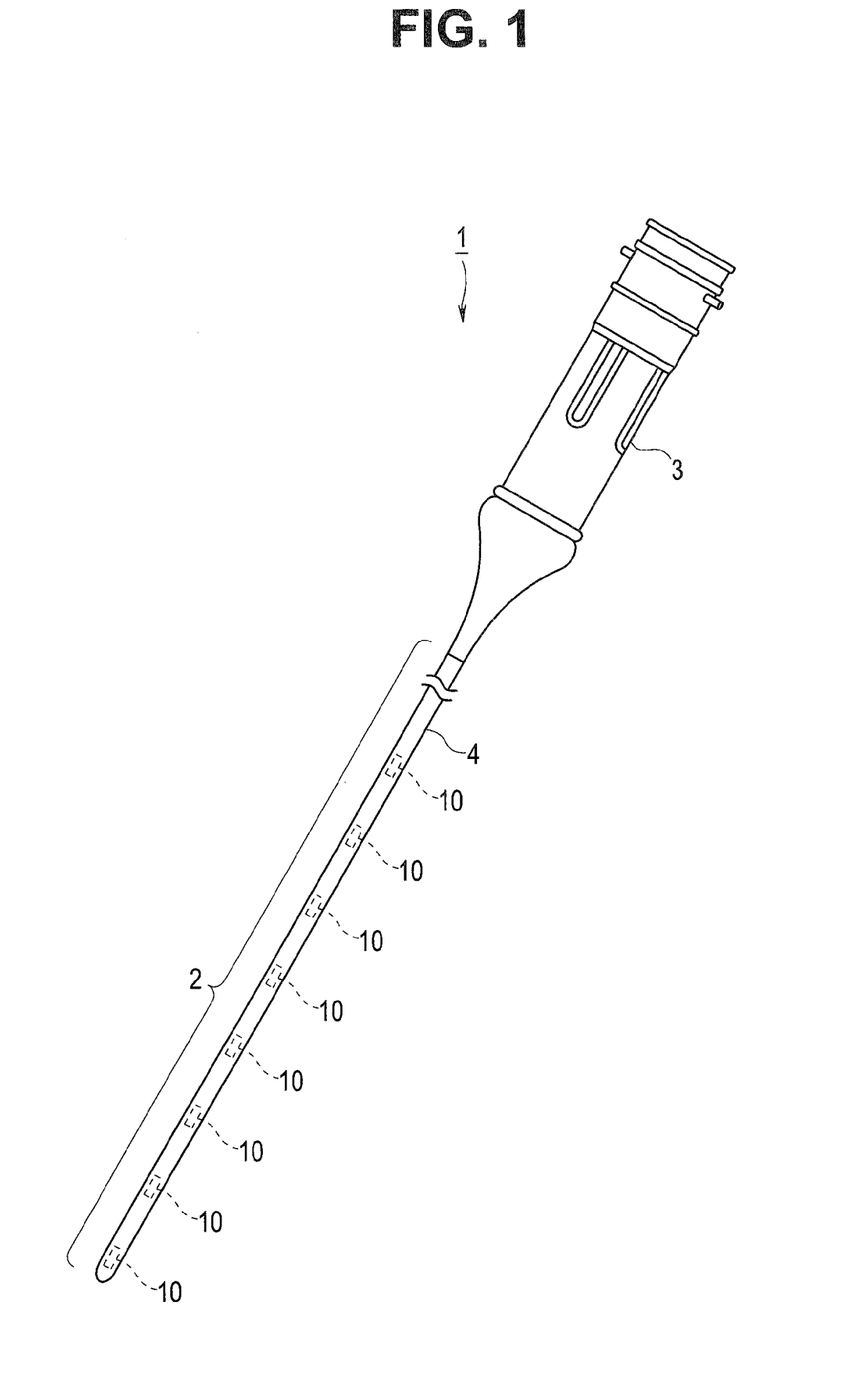
FIG. 1 is a perspective view showing an overall configuration of an endoscope insertion shape observation probe in an aspect of the present invention.
Figure 2:
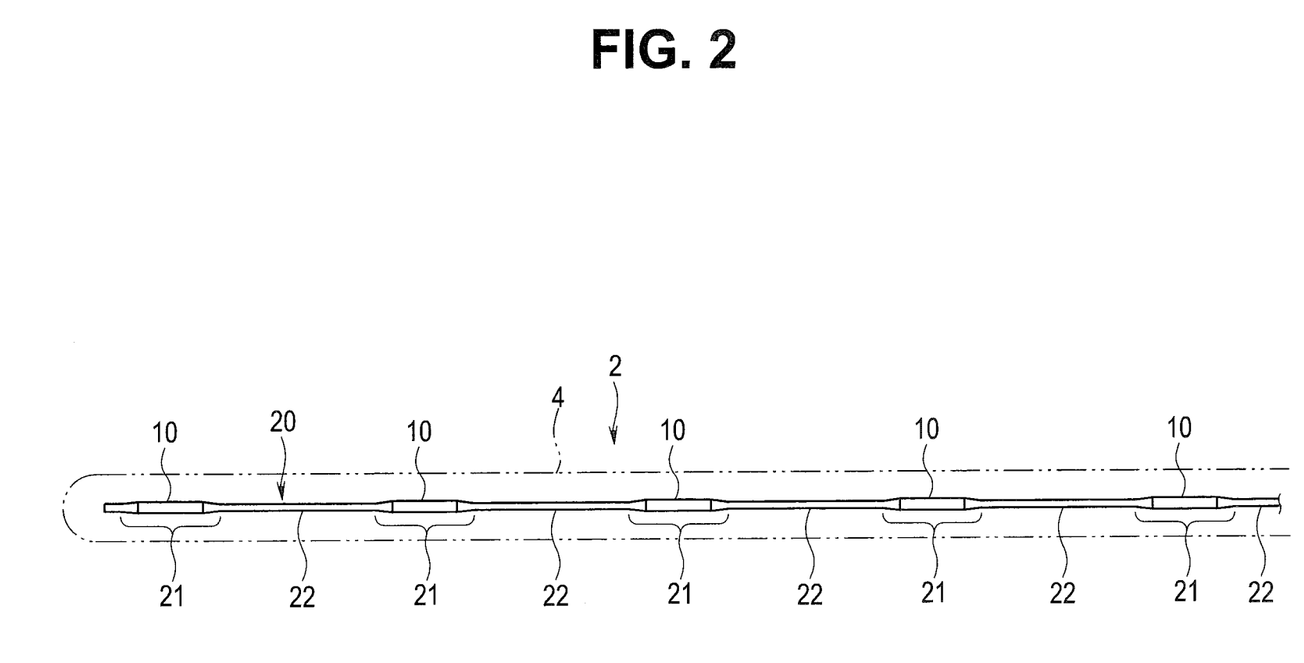
FIG. 2 is a plan view showing a configuration of a coil-unit housing member of the endoscope insertion shape observation probe disposed in an insertion section in the aspect.
Figure 3:
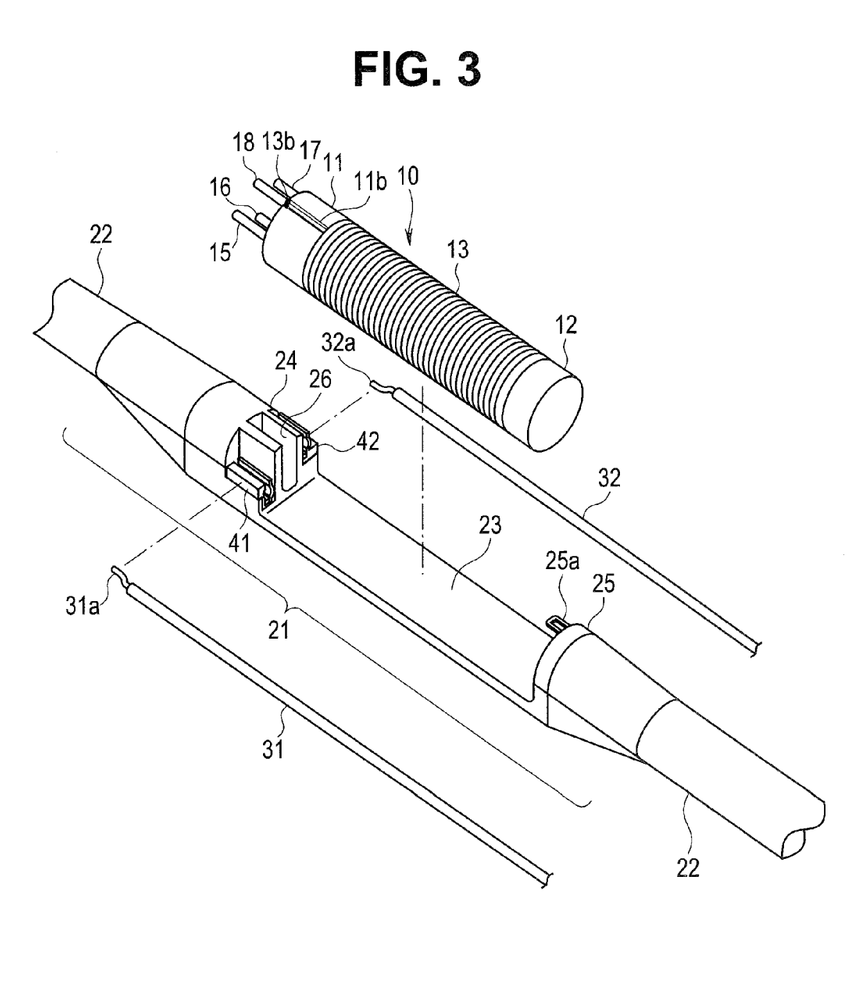
FIG. 3 is an exploded perspective view showing a configuration of a coil unit of the coil-unit housing member and a coil-unit housing section to which the coil unit is attached in the aspect.
Figure 4:
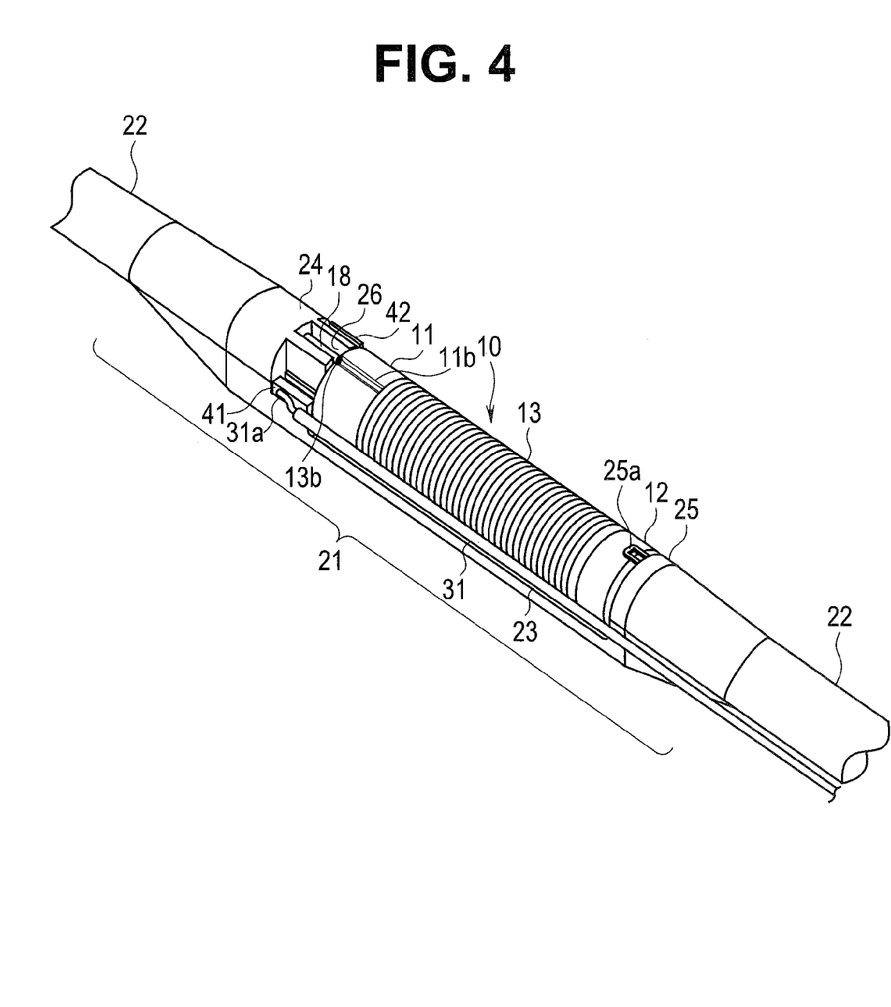
FIG. 4 is a perspective view showing a configuration of the coil-unit housing section attached with the coil unit in the aspect.
Figure 5:
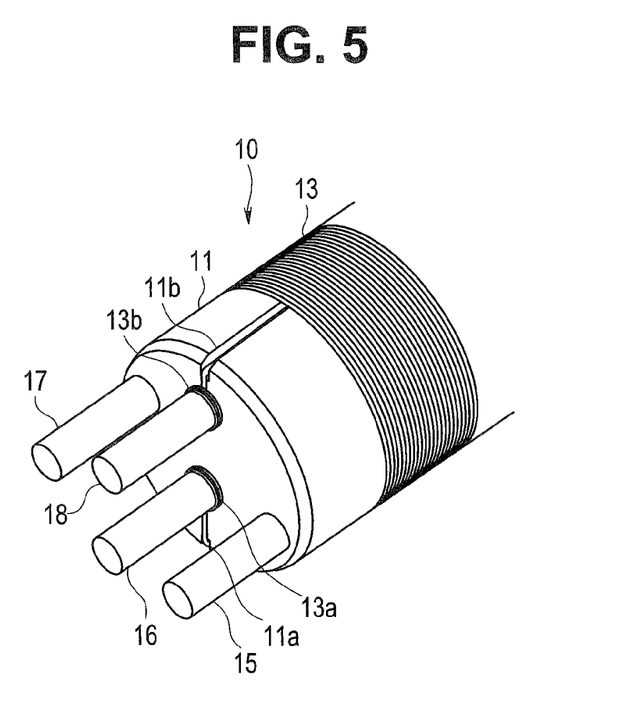
FIG. 5 is a perspective view showing a distal end portion of the coil unit provided with a connection terminal in the aspect.
Figure 6:
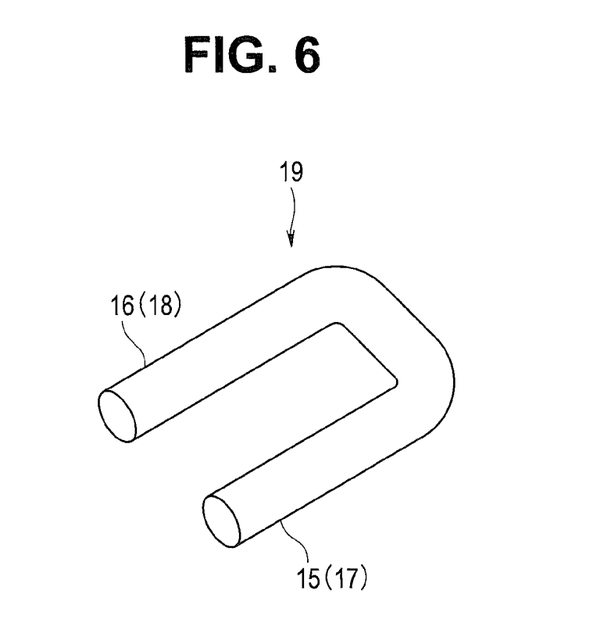
FIG. 6 is a perspective view showing a configuration of the connection terminal in the aspect.
Figure 7:
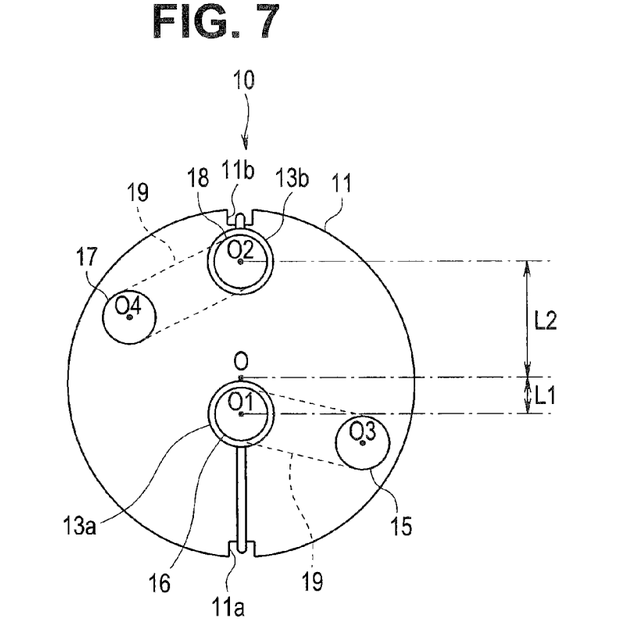
FIG. 7 is a front view showing a configuration of the coil unit provided with the connection terminal in the aspect.
Figure 8:
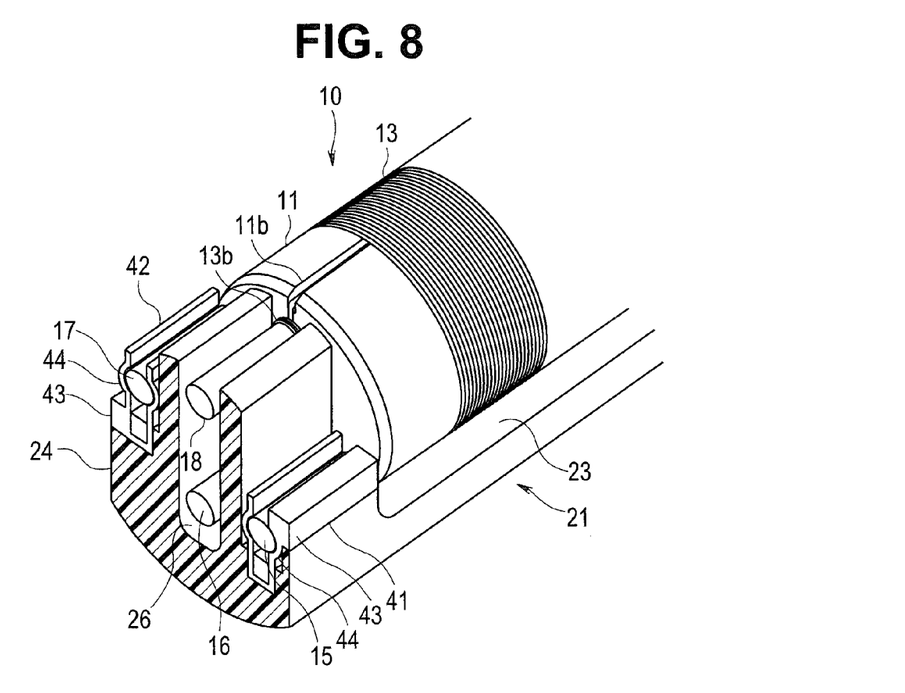
FIG. 8 is a perspective view showing a configuration of the coil unit and a distal end portion of the coil unit housing section in a state in which the coil unit is attached in the aspect.
Figure 9:
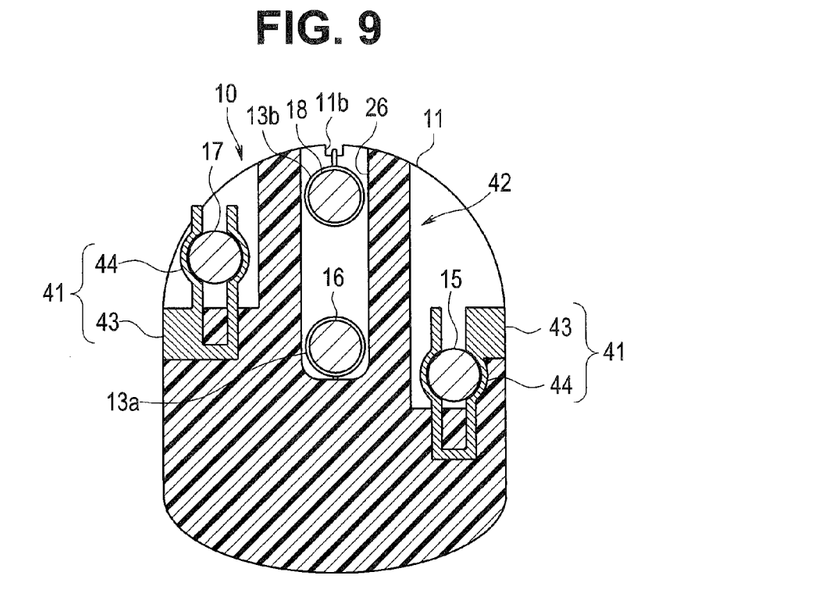
FIG. 9 is a sectional view of the coil-unit housing section in a state in which the coil unit is attached in a predetermined direction in the aspect.
Figure 10:
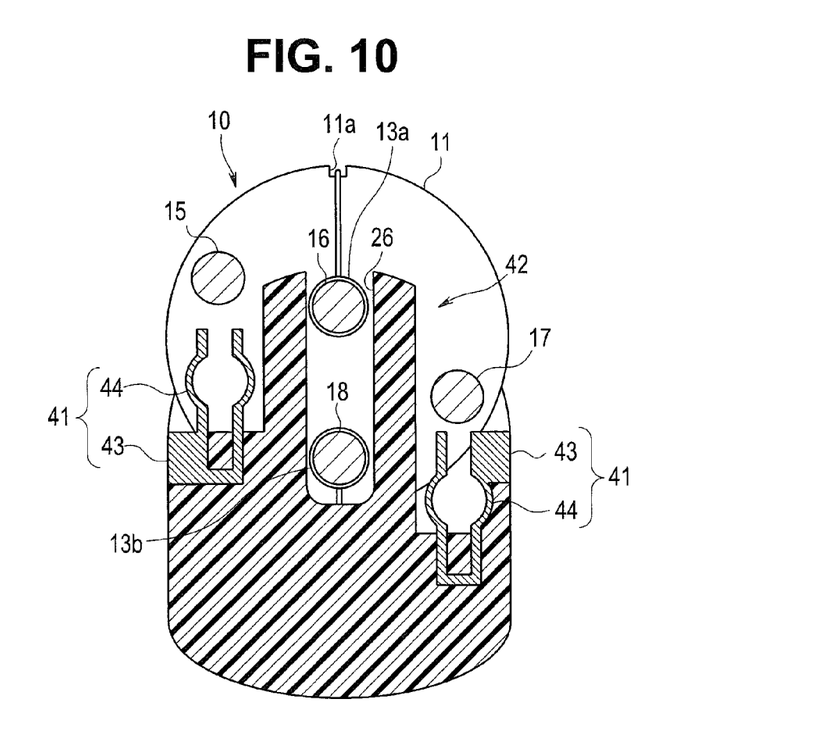
FIG. 10 is a sectional view of the coil-unit housing section in the case in which the coil unit is not attached in the predetermined direction in the aspect.

FIG. 1 is a perspective view showing an overall configuration of an endoscope insertion shape observation probe in an aspect of the present invention. FIG. 2 is a plan view showing a configuration of a coil-unit housing member of the endoscope insertion shape observation probe disposed in an insertion section. FIG. 3 is an exploded perspective view showing a configuration of a coil unit of the coil-unit housing member and a coil-unit housing section to which the coil unit is attached. FIG. 4 is a perspective view showing a configuration of the coil-unit housing section attached with the coil unit. FIG. 5 is a perspective view showing a distal end portion of the coil unit provided with a connection terminal. FIG. 6 is a perspective view showing a configuration of the connection terminal. FIG. 7 is a front view showing a configuration of the coil unit provided with the connection terminal. FIG. 8 is a perspective view showing a configuration of the coil unit and a distal end portion of the coil unit housing section in a state in which the coil unit is attached. FIG. 9 is a sectional view of the coil-unit housing section in a state in which the coil unit is attached in a predetermined direction. FIG. 10 is a sectional view of the coil-unit housing section in the case in which the coil unit is not attached in the predetermined direction.

A probe 1 shown in FIG. 1 in the present embodiment is an endoscope insertion shape observation probe (hereinafter simply abbreviated as probe) functioning as a medical probe. The probe 1 is insertable through a treatment instrument channel provided in a not-shown endoscope insertion section. Note that the probe 1 inserted through the treatment instrument channel and used is illustrated. However, components explained below may be incorporated in the endoscope insertion section itself.

The probe 1 includes, on a distal end side, an insertion section 2 in which a plurality of coil units 10, which are electronic components, are housed. An electric connector section 3 is provided on a proximal end side of the insertion section 2. The insertion section 2 of the probe 1 is an elongated soft medical instrument configured with an outer circumferential section covered by a sheath member 4 functioning as an outer skin formed of resin having biocompatibility such as polytetrafluoroethylene.

The electric connector section 3 of the probe 1 is electrically connected to an endoscope insertion shape observation apparatus (not shown in the figure). The endoscope insertion shape observation apparatus (not shown in the figure) calculates positions in a three-dimensional space of the respective coil units 10 from a detected magnetic field, determines a shape of the endoscope insertion section according to positions of a plurality of magnetic coils and estimation of positions among the coils, and displays the shape on a monitor.

As shown in FIG. 2, in the insertion section 2 of the probe 1, a coil-unit housing member (hereinafter referred to as housing member) 20, which is an electronic-component housing member that houses the plurality of coil units 10, is disposed. The housing member 20 is made of elongated solid silicon rubber or relatively soft resin such as polypropylene. The plurality of coil units 10 are detachably mountable on the housing member 20. Note that the housing member 20 may be covered by a heat shrinkage tube not shown in the figure.

The housing member 20 is formed by integral molding using a molding technique such as injection molding. Coil-unit housing sections (hereinafter referred to as housing sections) 21, which are a plurality of electronic-component housing sections that respectively house the coil units 10, are disposed at a predetermined interval via coupling sections 22 functioning as elongated shaft members.

The housing section 21 includes, as shown in FIG. 3 and FIG. 4, a bottom section 23 functioning as an electronic-component mounting section having a recessed shape formed in a part of the housing member 20. The bottom section 23 is provided flat between a distal-end-side wall section 24 on a distal end side and a proximal-end-side wall section 25 on a proximal end side. Note that a cross section of the bottom section 23 may be formed in an arcuate recessed shape according to an external shape of the coil unit 10.

That is, the housing section 21 includes the bottom section 23 and the distal-end-side wall section 24 and the proximal-end-side wall section 25 erected to an upward direction side from the bottom section 23 at both ends in a longitudinal direction of the bottom section 23.

More specifically, in order to house the coil unit 10, which is the electronic component, having a predetermined length and a predetermined height, the housing section 21 is formed in the recessed shape including the bottom section 23 having length substantially equal to the predetermined length in the longitudinal direction of the insertion section 2 of the probe 1 and the distal-end-side and proximal-end-side wall sections 24 and 25 erected at height substantially equal to the predetermined height of the coil unit 10 from the bottom section 23 at both the ends of the bottom section 23 in the longitudinal direction of the insertion section 2. Further, in the housing section 21, the bottom section 23 and the distal-end-side and proximal-end-side wall sections 24 and 25 are integrally formed.

In this way, a recess functioning as a housing space for housing the coil unit 10 is formed by a bottom surface of the bottom section 23 and opposed two wall surfaces of the distal-end-side and proximal-end-side wall sections 24 and 25. Note that coupling sections 22 extend in the longitudinal direction of the insertion section 2 of the probe 1 from the distal-end-side and proximal-end-side wall sections 24 and 25 and connect a plurality of housing sections 21.

In the distal-end-side wall section 24, a groove section 26 is formed from an upper center toward the bottom section 23 side. A pair of electric connection sections 41 and 42 is disposed at both ends across a sidewall forming the groove section 26. Core wires 31a and 32a of signal lines 31 and 32 for applying/feeding back an electric current to the coil unit 10 are electrically connected to the pair of electric connection sections 41 and 42 from both sides by brazing of a brazing material such as solder. Note that the pair of electric connection sections 41 and 42 is explained in detail below.

The proximal-end-side wall section 25 is disposed such that a claw section 25a, which comes into contact with and catches a proximal end upper section of the coil unit 10 housed in the housing section 21, projects from the upper center to the distal end side. That is, the claw section 25a is formed in a claw structure for preventing the coil unit 10 mounted on the housing section 21 from coming off.

A configuration of the coil unit 10 is explained in detail below.

The coil unit 10 functioning as an electronic component has a columnar shape as a whole and includes a magnetic coil (hereinafter simply referred to as coil) 13 obtained by winding a thin lead wire of copper or the like around a not-shown iron core, a distal-end-side insulating section 11 and a proximal-end-side insulating section 12 provided at both end portions of the coil 13, and a round bar-like plurality of, that is, four terminal sections 15 to 18 provided to project from a distal end face of the distal-end-side insulating section 11.

In the distal-end-side insulating section 11, two long grooves 11a and 11b (see FIG. 5 and FIG. 7), in which end portions 13a and 13b of the lead wire configuring the coil 13 are disposed to lead the lead wire to the distal end face, are formed in two parts on an outer circumferential section (upper and lower parts as viewed toward a paper surface).

Note that one end portion 13a of the lead wire is electrically connected to be wound around (bound to) a base of the terminal section 16 projecting from a position on a lower side as viewed toward the paper surface of FIG. 5 and FIG. 7 on the distal end face of the distal-end-side insulating section 11, that is, an attaching direction side of the coil unit 10 to the housing section 21 among the four terminal sections 15 to 18.

The other end portion 13b of the lead wire is electrically connected to be wound around (bound to) a base of the terminal section 18 projecting from a position on an upper side as viewed toward the paper surface of FIG. 5 and FIG. 7 on the distal end face of the distal-end-side insulating section 11, that is, an opposite side of the attaching direction side of the coil unit 10 to the housing section 21 among the four terminal sections 15 to 18.

Note that the end portions 13a and 13b of the lead wire are respectively connected to a pair of terminal sections 16 and 18 by brazing of solder or the like not to be loosened. The terminal section 16, to which the end portion 13a of the lead wire is connected, is electrically connected to the terminal section 15 functioning as a current apply side electrode.

Note that the terminal section 18, to which the end portion 13b of the lead wire is connected, is electrically connected to the terminal section 17 functioning as a current feedback side electrode. That is, among the four terminal sections 15 to 18, the terminal section 15 conducting to the terminal section 16 and the terminal section 17 conducting to the terminal section 18 configure a pair of electric connection terminal sections.

The two terminal sections 16 and 18 forming a pair provided in parallel in an up-down direction on the distal end face of the distal-end-side insulating section 11, that is, the attaching direction of the coil unit 10 to the housing section 21 are housed in the groove section 26 of the distal-end-side wall section 24 (see FIG. 8) when the coil unit 10 is mounted on the housing section 21. Consequently, the mounting direction around the longitudinal axis of the coil unit 10 is defined.

Note that, as explained above, the four terminal sections 15 to 18 are formed from a C-shaped conductor member 19 obtained by forming a pair of each of the two terminal sections 15 and 16 and each of the two terminal sections 17 and 18 as shown in FIG. 6. That is, in the coil unit 10, as shown in FIG. 7, two conductor members 19 are embedded in the distal-end-side insulating section 11. Consequently, the four terminal sections 15 to 18 are configured by the two conductor members 19 having the same shape.

As shown in FIG. 7, centers O1 and O2 of the respective two terminal sections 16 and 18, to which the end portions 13a and 13b of the lead wire housed in the groove section 26 of the distal-end-side wall section 24 are respectively connected, are respectively disposed in positions of different separation distances from a center (a center of the distal end face of the distal-end-side insulating section 11) O of the coil unit 10.

More specifically, the terminal section 16, to which the end portion 13a of the lead wire is connected, has the center O1 in a position separating from the center O of the distal end face of the coil unit 10 by length L1. On the other hand, the terminal section 18, to which the end portion 13b of the lead wire is connected, has the center O2 in a position separating from the center O of the distal end face of the coil unit 10 by length L2 larger than the length L1, which is the separation distance of the terminal section 16, to be further apart than the center O1 (L1<L2).

That is, in the distal-end-side insulating section 11 of the coil unit 10, the terminal section 16 is disposed in a position which is close to the center O of the distal end face of the coil unit 10 and the terminal section 18 is disposed in a position which is far from the center O of the distal end face of the coil unit 10.

The terminal sections 15 and 17 configuring a pair of electric connection terminal sections, to which the end portions 13a and 13b of the lead wire are electrically connected via the terminal sections 16 and 18, have centers O3 and O4 in positions point-symmetrical with respect to the center O of the distal end face of the coil unit 10, that is, rotated 180 degrees about the center O set as a point of symmetry.

The pair of electric connection sections 41 and 42 provided on both sides (a left-right direction as viewed toward paper surface of FIG. 8 and FIG. 9) of the distal-end-side insulating section 11 is explained in detail below.

As shown in FIG. 8 and FIG. 9, the pair of electric connection sections 41 and 42 is conductor members substantially C-shaped in section including rectangular block-like core-wire connecting sections 43, to which the core wires 31a and 32a of the signal lines 31 and 32 are connected, and a terminal engaging sections 44 in which semicircular sections are disposed to be opposed to each other such that the terminal sections 15 and 17 provided in the distal-end-side insulating section 11 of the coil unit 10 respectively engage with the terminal engaging sections 44.

In the pair of core-wire connecting sections 43, as shown in FIG. 3 and FIG. 4, the core wires 31a and 32a of the signal lines 31 and 32 are electrically connected to a plane section facing outward, which is a side portion of the coil unit 10, by brazing of solder or the like.

Note that the signal lines 31 and 32 respectively electrically connected to the core-wire connecting sections 43 of the pair of electric connection sections 41 and 42 are extended toward the proximal end side of the probe 1. The signal lines 31 and 32 are disposed to the electric connector section 3 of the probe 1.

In one electric connection section 41, the core-wire connecting section 43 is provided further on an upper part side than the terminal engaging section 44. On the other hand, in the other electric connection section 42, the core-wire connecting section 43 is provided further on a lower part side than the terminal engaging section 44.

In the distal-end-side insulating section 11, one electric connection section 41 is disposed further on the lower side than the other electric connection section 42. Therefore, the respective core-wire connecting sections 43 of the pair of electric connection sections 41 and 42 are provided in positions at substantially same heights in a side portion of the distal-end-side insulating section 11.

Consequently, the signal lines 31 and 32 are electrically connected to the core-wire connecting sections 43 in the positions at the substantially same heights in the side portion of the distal-end-side insulating section 11.

Note that an electric current is applied from one of the pair of electric connection sections 41 and 42 and the electric current is fed back from the other. That is, one of the signal lines 31 and 32 connected to the pair of electric connection sections 41 and 42 is a current application cable and the other is a current feedback cable.

A state in which the coil unit 10 is mounted on the housing section 21 is explained in detail below.

In the coil unit 10, as shown in FIG. 8, during the mounting on the housing section 21, the two terminal sections 16 and 18 projecting from up-down direction of the distal end face of the distal-end-side insulating section 11 are engaged into the groove section 26 formed in the distal-end-side wall section 24 of the housing section 21. That is, the two terminal sections 16 and 18 configure attaching-direction defining terminal sections engaged into the groove section 26 formed in the distal-end-side wall section 24 to define an attaching direction around the longitudinal axis of the coil unit 10.

In this state, as shown in FIG. 9, the pair of terminal sections 15 and 17, which projects from a left-right direction of the distal end face of the distal-end-side insulating section 11 and to which the end portions 13a and 13b of the lead wire are electrically connected via the terminal sections 16 and 18, is electrically connected to the pair of electric connection sections 41 and 42 in a state in which the terminal sections 15 and 17 are respectively fit and engaged in the terminal engaging sections 44 of the pair of electric connection sections 41 and 42 respectively provided in the distal-end-side wall section 24 and held by the terminal engaging sections 44.

Further, in the coil unit 10, as shown in FIG. 4, an outer circumferential surface upper portion of the proximal-end-side insulating section 12 is set in contact with and held by the claw section 25a projecting from the proximal-end-side wall section 25.

In this way, in the coil unit 10, the pair of terminal sections 15 and 17 on the distal end side is held by the terminal engaging sections 44 of the pair of electric connection sections 41 and 42 and the proximal end side is held by the claw section 25a provided in the proximal-end-side wall section 25. Consequently, the coil unit 10 is configured to be prevented from coming off the housing section 21.

That is, in the coil unit 10, the pair of terminal sections 15 and 17 on the distal end side is respectively mechanically held by the terminal engaging sections 44 of the pair of electric connection sections 41 and 42 and, on the proximal end side, the proximal-end-side insulating section 12 is also mechanically held by the claw section 25a provided in the proximal-end-side wall section 25. Consequently, the coil unit 10 is configured to be prevented from coming off the housing section 21.

The coil unit 10 can be easily detached from the housing section 21 by pulling out the pair of terminal sections 15 and 17 on the distal end side from the terminal engaging sections 44 of the pair of electric connection sections 41 and 42 and disconnecting the proximal-end-side insulating section 12 from the claw section 25a provided in the proximal-end-side wall section 25.

Further, in the coil unit 10, as explained above, one terminal section 16 housed from the center O of the distal end face in the groove section 26 of the distal-end-side wall section 24 is disposed close to the center O of the distal end face of the coil unit 10 and the other terminal section 18 is disposed in the position far from the center O of the distal end face of the coil unit 10.

Therefore, for example, as shown in FIG. 10, when the coil unit 10 is attached to the housing section 21 in a wrong direction rotated 180 degrees around the longitudinal axis, even if the two terminal sections 16 and 18 are engaged into the groove section 26, before the pair of terminal sections 15 and 17 fits in the terminal engaging sections 44 of the pair of electric connection sections 41 and 42, the terminal section 18 on the lower side comes into contact and interferes with a bottom surface of the groove section 26. The pair of terminal sections 15 and 17 cannot engage with the terminal engaging sections 44 and cannot be electrically connected to the pair of electric connection sections 41 and 42. Consequently, the coil unit 10 is prevented from being erroneously attached to the housing section 21.

In the probe 1 in the present embodiment explained above, compared with the conventional configuration, since the plurality of coil units 10 are mounted on the respective housing sections 21 of the insertion section 2, the plurality of coil units 10 can be set in accurate positions and assemblability is improved.

Further, in the probe 1, even if a deficiency occurs in one of the coil units 10, it is sufficient to detach the coil unit 10 to be replaced from the housing section 21 and mount a new coil unit 10 on the housing section 21. Therefore, maintainability is improved. Consequently, even if a deficiency occurs in one of the coil units 10, it is unnecessary to replace the entire probe 1. Therefore, maintenance costs decrease.

Consequently, the probe 1 in the present embodiment can be configured such that setting of the plurality of coil units 10 is simplified and assemblability and maintainability are improved and maintenance costs can be reduced.

MODIFICATIONS

Note that the coil unit 10 mounted on the housing section 21 of the probe 1 may be configured as indicated by modifications explained below.

Figure 11:
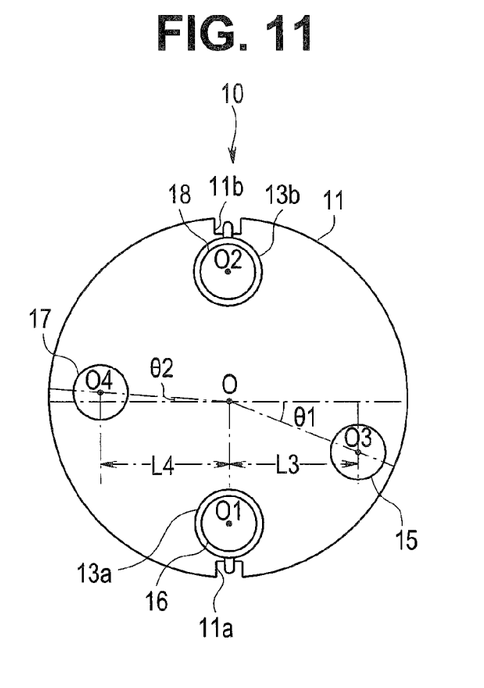
FIG. 11 is a front view showing a configuration of the coil unit in which a connection terminal is provided in a first modification.
Figure 12:
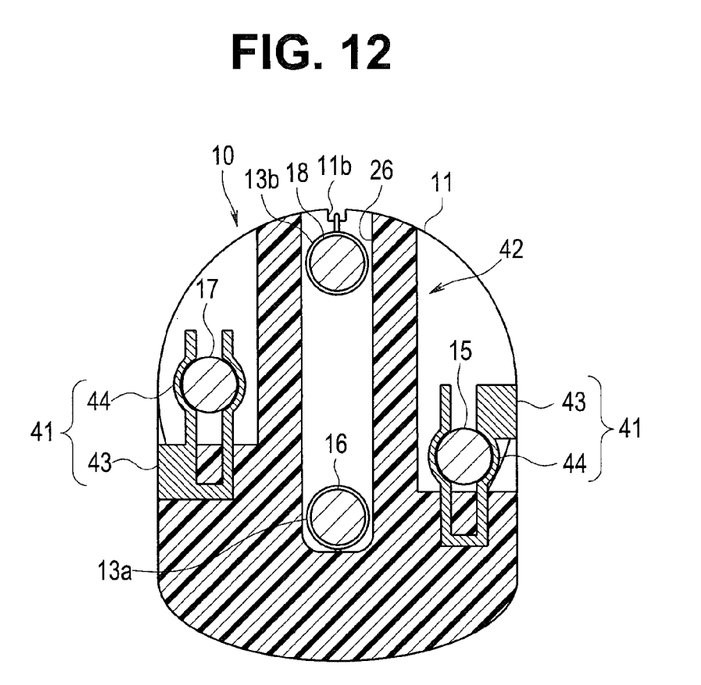
FIG. 12 is a sectional view of the coil-unit housing section in a state in which the coil unit in the first modification is attached in a predetermined direction.
Figure 13:
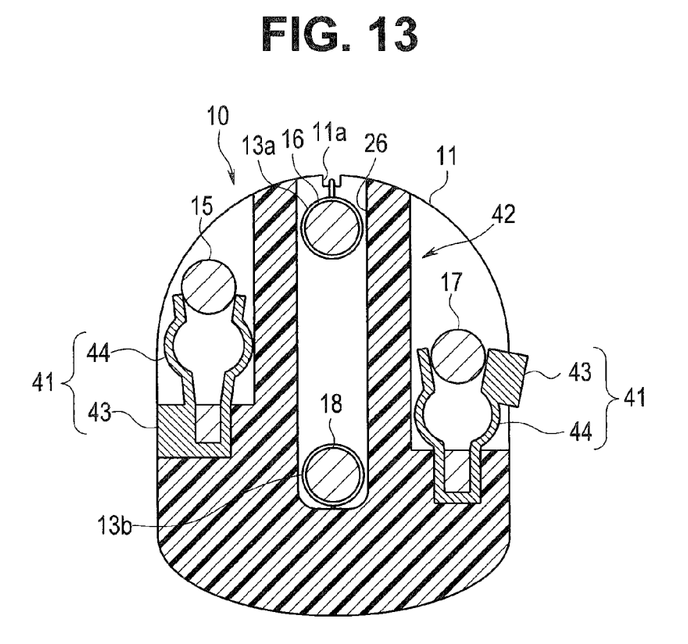
FIG. 13 is a sectional view of the coil-unit housing section in the case in which the coil unit in the first modification is not attached in the predetermined direction.
Figure 14:
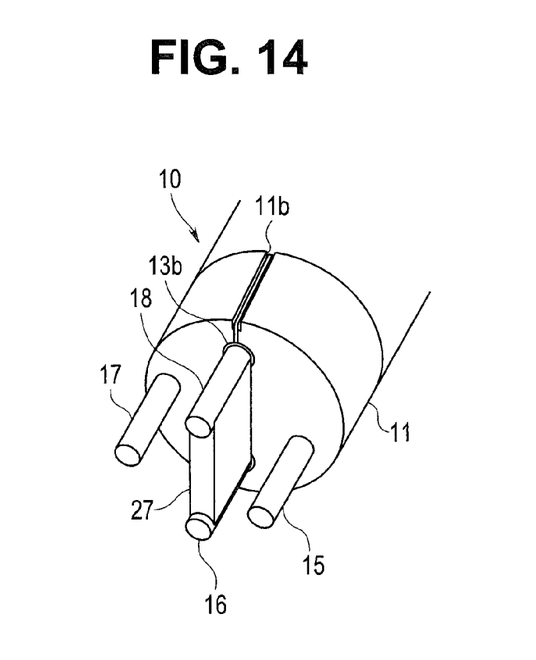
FIG. 14 is a partial perspective view showing a configuration in which a wall section is provided to connect terminal sections of the coil unit in a second modification.
Figure 15:
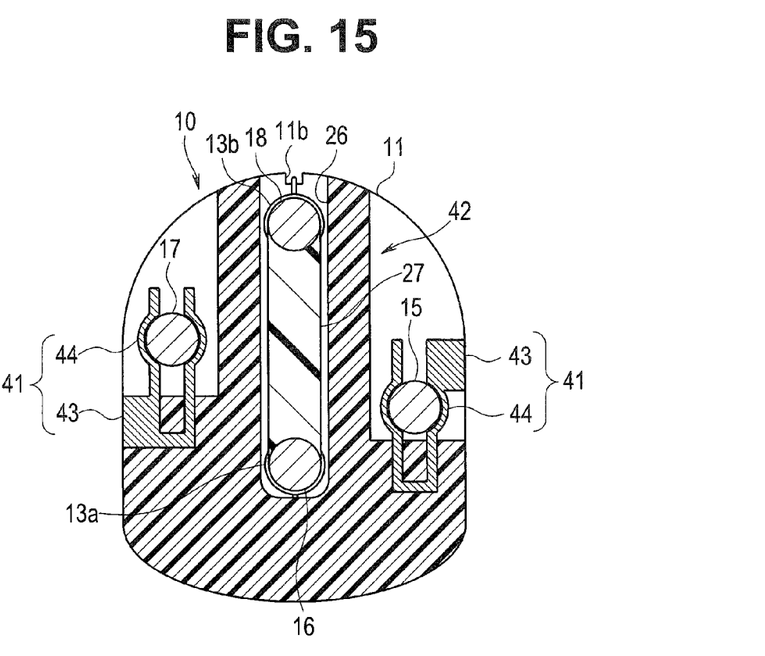
FIG. 15 is a sectional view of the coil-unit housing section in a state in which the coil unit in the second modification is attached.
Figure 16:
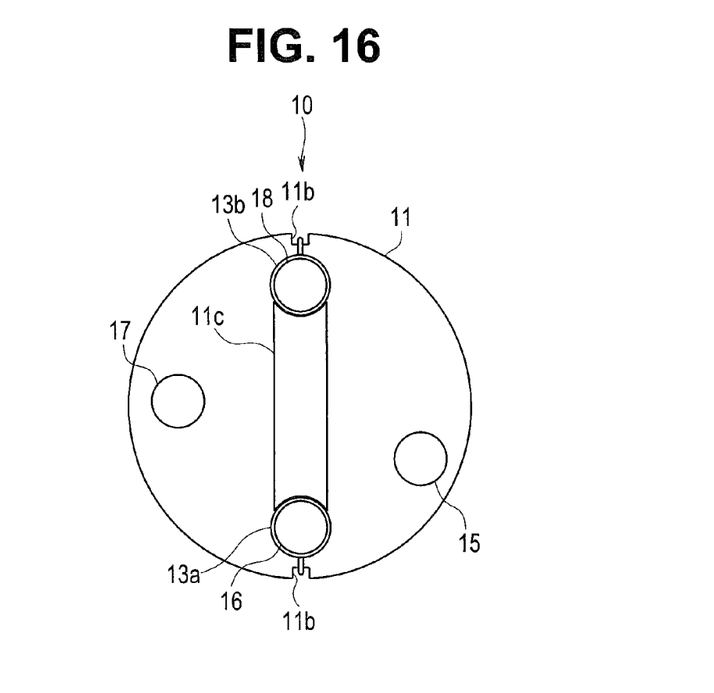
FIG. 16 is a front view showing a configuration in which a wall section is provided between the terminal sections of the coil unit in a third modification.

FIG. 11 is a front view showing a configuration of the coil unit in which a connection terminal is provided in a first modification. FIG. 12 is a sectional view of the coil-unit housing section in a state in which the coil unit in the first modification is attached in a predetermined direction. FIG. 13 is a sectional view of the coil-unit housing section in the case in which the coil unit in the first modification is not attached in the predetermined direction. FIG. 14 is a partial perspective view showing a configuration in which a wall section is provided to connect terminal sections of the coil unit in a second modification. FIG. 15 is a sectional view of the coil-unit housing section in a state in which the coil unit in the second modification is attached. FIG. 16 is a front view showing a configuration in which a wall section is provided between the terminal sections of the coil unit in a third modification.

First Modification

In the coil unit 10 in this modification, as shown in FIG. 11, the two terminal sections 16 and 18 housed in the groove section 26 of the distal-end-side wall section 24 have the centers O1 and O2 in positions point-symmetrical with respect to the center O of the distal end face of the coil unit 10, that is, rotated 180 degrees about the center O set as a point of symmetry.

The centers O3 and O4 of the pair of terminal sections 15 and 17, to which the end portions 13a and 13b of the lead wire are electrically connected via the terminal sections 16 and 18, are disposed in positions where separation distances in a horizontal direction (left and right lateral directions) from the center O of the distal end face of the coil unit 10, that is, a direction orthogonal to the attaching direction of the coil unit 10 to the housing section 21 are equal.

More specifically, one terminal section 15 has the center O3 in a position separating from the center O of the distal end face of the coil unit 10 by length L3 in a direction orthogonal to the attaching direction to the housing section 21 (i.e., a right side as viewed toward paper surface), that is, a position of a predetermined angle θ1 around the center O (a clockwise direction).

On the other hand, the other terminal section 17 has a center O4 in a position separating from the center O of the distal end face of the coil unit 10 by length L4 equal to the length L3 (L3=L4) in a direction orthogonal to the attaching direction to the housing section 21 (a left side as viewed toward the paper surface), that is, a position of a predetermined angle θ2 smaller than the predetermined angle θ1 (θ1>θ2) around the center O (in a clockwise direction).

That is, unlike the terminal sections 16 and 18, the pair of terminal sections 15 and 17 does not have the centers O3 and O4 in positions point-symmetrical with respect to the center O of the distal end face of the coil unit 10, that is, rotated 180 degrees about the center O set as a point of symmetry.

In the coil unit 10 in this modification configured as explained above, as shown in FIG. 12, during the mounting on the housing section 21, the two terminal sections 16 and 18 are engaged into the groove section 26 formed in the distal-end-side wall section 24 of the housing section 21.

In this state, the pair of terminal sections 15 and 17 is electrically connected to the pair of electric connection sections 41 and 42 in a state in which the terminal sections 15 and 17 are fit and engaged in the terminal engaging sections 44 of the pair of electric connection sections 41 and 42 and held by the terminal engaging sections 44.

As in the embodiment, in the coil unit 10, the outer circumferential upper portion of the proximal-end-side insulating section 12 is set in contact with and held by the claw section 25a (see FIG. 4) projecting from the proximal-end-side wall section 25.

In this way, in the coil unit 10 in this modification, the pair of terminal sections 15 and 17 on the distal end side is held by the terminal engaging sections 44 of the pair of electric connection sections 41 and 42 and the proximal end side is held by the claw section 25a provided in the proximal-end-side wall section 25. Consequently, the coil unit 10 is configured to be prevented from coming off the housing section 21.

The coil unit 10 can be easily detached from the housing section 21 by pulling out the pair of terminal sections 15 and 17 on the distal end side from the terminal engaging sections 44 of the pair of electric connection sections 41 and 42 and disconnecting the proximal-end-side insulating section 12 from the claw section 25a provided in the proximal-end-side wall section 25.

Further, in the coil unit 10, as explained above, unlike the terminal sections 16 and 18, the pair of terminal sections 15 and 17 does not have the centers O3 and O4 in positions point-symmetrical with respect to the center O of the distal end face of the coil unit 10, that is, rotated 180 degrees about the center O set as a point of symmetry.

Therefore, for example, as shown in FIG. 13, when the coil unit 10 is attached to the housing section 21 in a wrong direction rotated 180 degrees around the longitudinal axis, in a state in which the two terminal sections 16 and 18 are engaged into the groove section 26, before the pair of terminal sections 15 and 17 fits in the terminal engaging sections 44 of the pair of electric connection sections 41 and 42, the terminal section 16 comes into contact and interferes with a bottom section of the groove section 26. The pair of terminal sections 15 and 17 cannot engage with the terminal engaging sections 44 and cannot be held by the pair of electric connection sections 41 and 42. Consequently, the coil unit 10 in this modification is prevented from being erroneously attached to the housing section 21.

Second Modification

In the coil unit 10 in this modification, as shown in FIG. 14, a nonconductive wall section 27 formed of resin or the like that connects the two terminal sections 16 and 18 housed in the groove section 26 of the distal-end-side wall section 24 is provided. In the wall section 27, a width dimension substantially the same as or equal to or smaller than a dimension in a width direction of the two terminal sections 16 and 18 is set.

In the coil unit 10 in this modification configured as explained above, as shown in FIG. 15, during the mounting on the housing section 21, when the two terminal sections 16 and 18 engage into the groove section 26 formed in the distal-end-side wall section 24 of the housing section 21, stable assembly can be performed because the wall section 27 is provided. Further, the terminal sections 16 and 18 can be easily distinguished from the pair of terminal sections 15 and 17 fit and engaged in the terminal engaging sections 44 of the pair of electric connection sections 41 and 42.

Third Modification

In the coil unit 10 in this modification, as shown in FIG. 16, a wall section 11c formed integrally with the distal-end-side insulating section 11 is provided between the two terminal sections 16 and 18 housed in the groove section 26 of the distal-end-side wall section 24. As in the second modification, in the wall section 11c, a width dimension substantially the same as or equal to or smaller than the dimension in the width direction of the two terminal sections 16 and 18 is set.

In the coil unit 10 in this modification configured as explained above, as in the second modification, during the mounting on the housing section 21, when the two terminal sections 16 and 18 engage into the groove section 26 formed in the distal-end-side wall section 24 of the housing section 21, stable assembly can be performed because the wall section 11c is provided. Further, the terminal sections 16 and 18 can be easily distinguished from the pair of terminal sections 15 and 17 fit and engaged in the terminal engaging sections 44 of the pair of electric connection sections 41 and 42.

The invention described in the respective embodiments explained above is not limited to the embodiments and the modifications. Besides, in an implementation stage, various modifications can be implemented in a range not departing from the spirit of the invention. Further, inventions in various stages are included in the embodiments. Various inventions can be extracted according to appropriate combinations in a plurality of constituent elements disclosed herein.

For example, when the problems to be solved by the invention can be solved and the effects mentioned in the summary of the invention can be obtained even if several constituent elements are deleted from all the constituent elements described in the embodiments, a configuration from which the constituent elements are deleted can be extracted as an invention.

What is claimed is:

1. An endoscope insertion shape observation probe that is elongatedly formed along a longitudinal axis direction and is insertable into a channel provided in an endoscope insertion section or is incorporated in the endoscope insertion section, the endoscope insertion shape observation probe comprising:
an electronic component;
a housing section having a recessed shape that detachably and attaachably houses the electronic component;
a pair of electric connection sections provided in the housing section;
a pair of electric connection terminal sections provided in the electronic component and engaged with and electrically connected to the electric connection sections, the electric connection terminal sections mechanically holding the electronic component when the detachable and attachable electronic component is attached to the housing section;
a groove section formed in the housing section; and
two attaching-direction defining terminal sections provided in the electronic component, the attaching-direction defining terminal sections engaging into the groove section and defining a direction around the longitudinal axis in which the electronic component is attached to the housing section.

2. The endoscope insertion shape observation probe according to claim 1, wherein the groove section and the attaching-direction defining terminal sections are provided on an end face opposed to the housing section in a longitudinal axis direction in the electronic component.

3. The endoscope insertion shape observation probe according to claim 2, wherein one or another of the pair of electric connection terminal sections and one or another of the two attaching-direction defining terminal sections are formed of conductor members having a same shape respectively forming a pair.

4. The endoscope insertion shape observation probe according to claim 1, wherein
the pair of electric connection terminal sections and the two attaching-direction defining terminal sections are provided to project from a distal end face in a longitudinal direction of the electronic component,
the pair of electric connection terminal sections is provided at one end of the electronic component to have a predetermined angle with respect to the direction in which the electronic component is attached to the housing section and have centers in point symmetrical positions with respect to a center of the distal end face, and
the two attaching-direction defining terminal sections are provided in parallel in the attaching direction of the electronic component to the housing section and provided at one end of the electronic component to have centers in positions where separation distances from the center of the distal end face are different from each other.

5. The endoscope insertion shape observation probe according to claim 1, wherein
the pair of electric connection terminal sections and the two attaching-direction defining terminal sections are provided to project from a distal end face in a longitudinal direction of the electronic component,
the pair of electric connection terminal sections is provided to one end of the electronic component to have centers in positions having different angles around a center of the distal end face with respect to a direction orthogonal to the attaching direction of the electronic component to the housing section, and
the two attaching-direction defining terminal sections are provided in parallel in the attaching direction of the electronic component to the housing section and provided at one end of the electronic component to have centers in positions point symmetrical with respect to the center of the distal end face.

6. The endoscope insertion shape observation probe according to claim 1, further comprising a claw section provided on an opposite side of the pair of electric connection sections of the housing section, the claw section holding the electronic component attached to the housing section in contact with an outer circumferential surface of the electronic component.

7. The endoscope insertion shape observation probe according to claim 1, wherein the pair of electric connection terminal sections is provided in both side portions of the housing section and includes core-wire connecting sections in which a plane section facing side-outward, to which communication cables that respectively apply/feed back an electric current to the electronic component are electrically connected, is formed.

* * * * *